(12) United States Patent
DeFalco et al.

(10) Patent No.: US 9,387,021 B2
(45) Date of Patent: Jul. 12, 2016

(54) IMPLANT WITH SEMI-ENCLOSED SCREWS

(75) Inventors: Anthony C. DeFalco, Andover, NJ (US); Rawley Stanhope, The Colony, TX (US)

(73) Assignee: EBI, LLC, Parsippany, NJ (US)

( * ) Notice: Subject to any disclaimer, the term of this patent is extended or adjusted under 35 U.S.C. 154(b) by 182 days.

(21) Appl. No.: 13/589,501

(22) Filed: Aug. 20, 2012

(65) Prior Publication Data
US 2014/0052255 A1 Feb. 20, 2014

(51) Int. Cl.
*A61F 2/44* (2006.01)
*A61B 17/80* (2006.01)
*A61F 2/46* (2006.01)
*A61F 2/30* (2006.01)

(52) U.S. Cl.
CPC ............ *A61B 17/8057* (2013.01); *A61F 2/447* (2013.01); *A61F 2/4611* (2013.01); *A61F 2002/305* (2013.01); *A61F 2002/3079* (2013.01); *A61F 2002/30387* (2013.01); *A61F 2002/30451* (2013.01); *A61F 2002/30774* (2013.01); *A61F 2002/30787* (2013.01); *A61F 2002/30836* (2013.01); *A61F 2002/30843* (2013.01); *A61F 2002/30859* (2013.01); *A61F 2002/30869* (2013.01); *A61F 2002/4475* (2013.01)

(58) Field of Classification Search
CPC .............. A61B 17/80; A61B 17/8057; A61B 17/1728; A61B 17/7059; A61B 17/8052; A61B 17/8605; A61B 17/863; A61F 2/44–2/447
USPC ................ 623/17.11–17.16; 606/280–299; 403/77; 411/437
See application file for complete search history.

(56) References Cited

U.S. PATENT DOCUMENTS

| 1,375,781 | A | * | 4/1921 | De Long ................. 411/437 |
| 3,038,366 | A | * | 6/1962 | Hindman ................ 411/433 |
| 4,083,288 | A | * | 4/1978 | Williams ............... 411/436 |
| 4,826,376 | A | * | 5/1989 | Aldridge et al. ........... 411/237 |
| 4,990,044 | A | * | 2/1991 | Kimak ................. 411/427 |
| 5,074,731 | A | * | 12/1991 | Schneider ............. 411/437 |
| 5,324,150 | A | * | 6/1994 | Fullerton ............. 411/433 |
| 5,403,136 | A | * | 4/1995 | Mathys ........... A61B 17/744 411/263 |
| 7,077,864 | B2 | * | 7/2006 | Byrd et al. ............ 623/17.11 |
| 7,661,915 | B2 | * | 2/2010 | Whipple .............. 411/151 |

(Continued)

FOREIGN PATENT DOCUMENTS

AU 2002220448 B2 7/2003
JP 2008206789 A 9/2008

(Continued)

OTHER PUBLICATIONS

Romanenko, K. K. et al., Funktsii i vidy plactin i vintov v sovremennom osteosinteze. Ortopediya, travmatologiya i protezirovanie, 2010, No. 1, p. 68-75. (with English abstract).

(Continued)

*Primary Examiner* — Jan Christopher Merene
*Assistant Examiner* — Steven Cotroneo
(74) *Attorney, Agent, or Firm* — Schwegman Lundberg & Woessner, P.A.

(57) ABSTRACT

The present teachings provide an implant. The implant can include an implant body partially defining at least one threaded aperture. The implant can also include a bone fastener including a threaded portion threadably engaged with the at least one threaded aperture. The threaded aperture can circumferentially surround no more than 180° of the bone fastener.

24 Claims, 4 Drawing Sheets

(56) References Cited

U.S. PATENT DOCUMENTS

| | | | |
|---|---|---|---|
| 8,372,152 B2* | 2/2013 | Kirschman | 623/17.16 |
| 8,622,679 B2* | 1/2014 | Jette | 411/437 |
| 8,794,882 B2* | 8/2014 | Whaley et al. | 408/221 |
| 2002/0120334 A1* | 8/2002 | Crozet | A61B 17/86 623/17.11 |
| 2006/0100623 A1* | 5/2006 | Pennig | 606/64 |
| 2006/0206208 A1* | 9/2006 | Michelson | 623/17.11 |
| 2010/0262193 A1* | 10/2010 | Frigg et al. | 606/281 |
| 2010/0274296 A1 | 10/2010 | Appenzeller et al. | |
| 2011/0009966 A1* | 1/2011 | Michelson | 623/17.11 |
| 2011/0301714 A1 | 12/2011 | Theofilos | |
| 2012/0109306 A1* | 5/2012 | Jacob et al. | 623/17.16 |
| 2012/0109308 A1* | 5/2012 | Lechmann et al. | 623/17.16 |
| 2012/0109309 A1* | 5/2012 | Mathieu et al. | 623/17.16 |
| 2012/0203348 A1 | 8/2012 | Michelson | |
| 2012/0215313 A1* | 8/2012 | Saidha et al. | 623/17.16 |

FOREIGN PATENT DOCUMENTS

| | | |
|---|---|---|
| JP | 2012115368 A | 6/2012 |
| WO | WO-03/055401 A1 | 7/2003 |

OTHER PUBLICATIONS

Wagnac, E. et al., Biomechanical analysis of pedicle screw placement: a feasibility study. Stud Health Technol Inform, 2010, 158, p. 167-171 (abstract) [online]. Retrieved from PubMed, PMID: 20543418.

International Search Report and Written Opinion of the ISA for PCT/US2013/055821, ISA/FIPS, Moscow, mailed Dec. 19, 2013.

Chinese Application Serial No. 2013800057107, Response filed Apr. 26, 2016 to Office Action mailed Dec. 11, 2015, with English translation of claims, 14 pgs.

European Application Serial No. 13831404.2, Extended European Search Report mailed Mar. 16, 2016, 9 pgs.

* cited by examiner

IMPLANT WITH SEMI-ENCLOSED SCREWS

INTRODUCTION

In general, the human musculoskeletal system is composed of a variety of tissues including bone, ligaments, cartilage, muscle, and tendons. Tissue damage or deformity stemming from trauma, pathological degeneration, or congenital conditions often necessitates surgical intervention to restore function. Surgical intervention can include any surgical procedure that can restore function to the damaged tissue, which can require the use of one or more orthopedic prosthesis, such as orthopedic nails, screws, implants, etc.

In one example, in order to restore function to a damaged portion of the spinal column, one or more implants can be coupled to the anatomy via one or more bone fasteners. For example, an implant can be positioned between and secured to adjacent vertebrae to repair a damaged spine. In another example, a plate can be secured to the anatomy to restore function to a damaged portion of the spine.

The present teachings relate to implants for use in repairing damaged tissue, and more specifically relate to an implant having semi-enclosed screws.

SUMMARY

According to various aspects, provided is an implant. The implant can include an implant body partially defining at least one threaded aperture. The implant can also include a bone fastener including a threaded portion threadably engaged with the at least one threaded aperture. The threaded aperture can circumferentially surround no more than 180 degrees)(° of the bone fastener.

Further provided is an implant, which can include an implant body partially defining at least one aperture. The at least one aperture can have an open perimeter and a first plurality of threads. The implant can include a bone fastener. The bone fastener can include a head having a second plurality of threads threadably engaged with the first plurality of threads of the at least one aperture. The first plurality of threads and the second plurality of threads can have interlocking thread forms.

Also provided is an implant, which can comprise an implant body. The implant body can partially define at least one aperture having a first interlocking thread form that circumferentially surrounds no more than 180° of the at least one aperture. The implant can include at least one bone fastener. The at least one bone fastener can include a head having a second interlocking thread form threadably engaged with the first interlocking thread form of the at least one aperture. A pitch of the first interlocking thread form can be different than a pitch of the second interlocking thread form.

Further areas of applicability will become apparent from the description provided herein. It should be understood that the description and specific examples are intended for purposes of illustration only and are not intended to limit the scope of the present teachings.

DRAWINGS

The drawings described herein are for illustration purposes only and are not intended to limit the scope of the present teachings in any way.

DESCRIPTION OF VARIOUS ASPECTS

The following description is merely exemplary in nature and is not intended to limit the present teachings, application, or uses. It should be understood that throughout the drawings, corresponding reference numerals indicate like or corresponding parts and features. Although the following description is related generally to a particular implant with semi-enclosed screws, it will be understood that the teachings associated with the semi-enclosed screws as described and claimed herein can be used in any appropriate surgical procedure, such as in a minimally invasive orthopedic fixation procedure. Therefore, it will be understood that the following discussions are not intended to limit the scope of the present teachings and claims herein.

With reference to FIGS. 1-5B, an implant 10 in accordance with the present teachings is shown. The implant 10 can include at least one bone fastener or bone screw 12. In one example, the implant 10 can include a first bone screw 12a and a second bone screw 12b. In certain applications, with reference to FIG. 1, the implant 10 can be positioned within an intervertebral disc space D, between adjacent vertebral bodies V to restore disc height and stabilize the vertebrae for long-term spinal fusion. It should be noted that although a single implant 10 will be described and illustrated herein as being positioned within an intervertebral disc space, multiple implants 10 could be used in various locations along the spinal column depending upon the selected procedure. In addition, the shape of the implant 10 described and illustrated herein is merely exemplary, as the implant 10 can have any desired shape for placement between the adjacent vertebrae, such as rectangular, circular, torodial, etc. It should also be noted that the implant 10 is merely exemplary, as any suitable implant could be employed with one or more of the first bone screw 12a and second bone screw 12b, such as a bone plate, as will be discussed further herein.

Figures 1, 2:
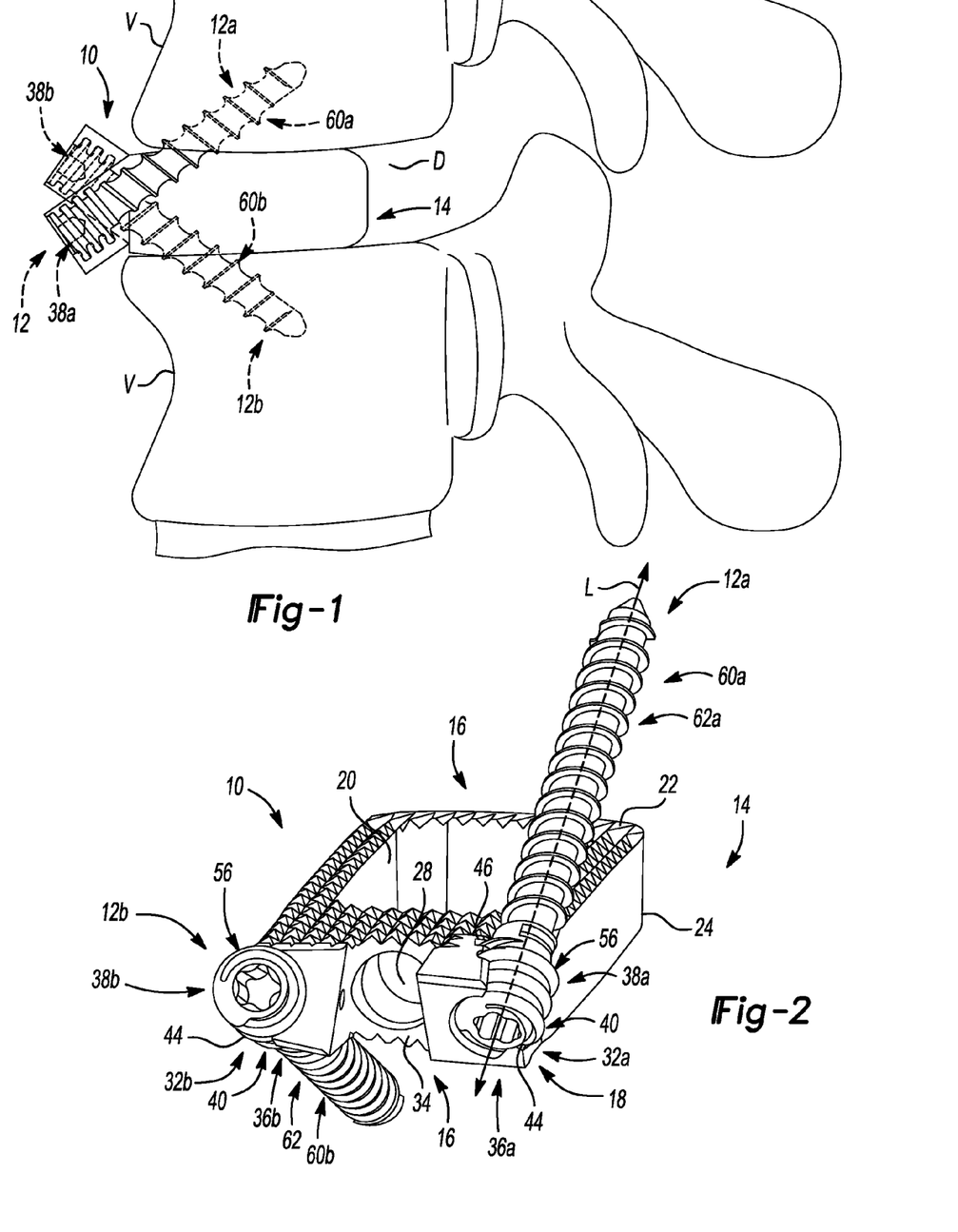
FIG. 1 is a schematic environmental illustration of an exemplary implant with semi-enclosed screws coupled to an anatomy according to the present teachings.
FIG. 2 is a perspective view of the implant of FIG. 1.
Figures 3, 4:
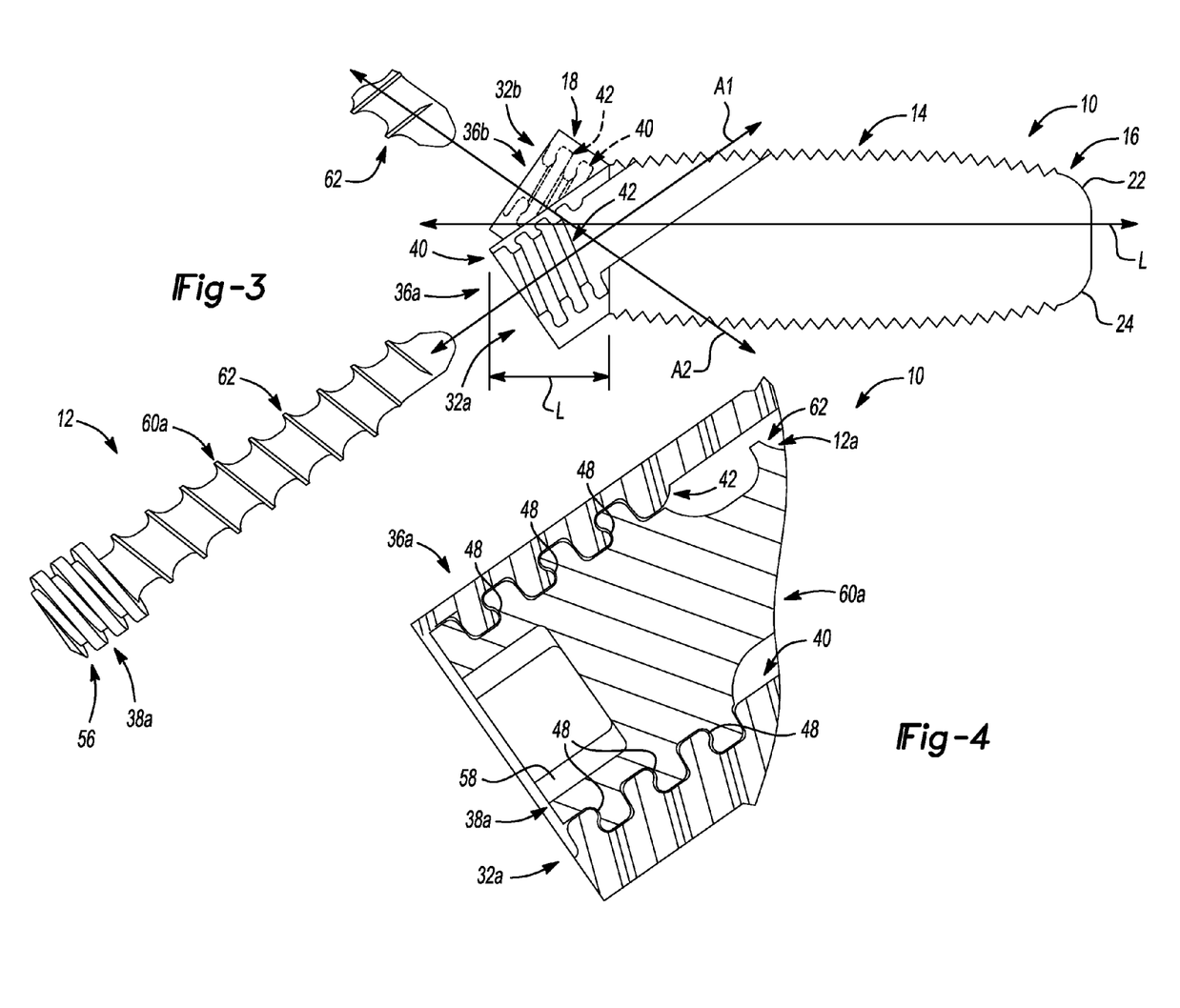
FIG. 3 is an exploded side view of the implant of FIG. 2.
FIG. 4 is a cross-sectional view of the implant of FIG. 2, taken along line 4-4 of FIG. 2.

With reference to FIGS. 2 and 3, the implant 10 can include a body 14. The body 14 of the implant 10 can be formed from any suitable biocompatible material, such as a biocompatible metal, metal alloy or polymer. For example, the body 14 can be composed of polyether ether ketone (PEEK), but the body 14 could also be formed of titanium or any other suitable material. The body 14 can have a generally rectangular shape, and can have a first end 16, a second end 18 and an aperture 20 (FIG. 2). The aperture 20 can cooperate with an insertion tool to enable the placement of the implant 10 within the anatomy. The aperture 20 can also be filled with a biocompatible material, if desired, such as a bone in-growth promoting agent, an antibiotic, etc. The body 14 can also include a plurality of teeth, if desired, to resist expulsion of the implant 10 from the anatomy.

The first end 16 can include a taper. The first end 16 can assist in distracting the adjacent vertebral bodies V during the insertion of the implant 10, and can assist in navigating the implant 10 through the anatomy. The first end 16 can include a first tapered surface 22 and a second tapered surface 24. The first tapered surface 22 can be generally opposite the second tapered surface 24.

With reference to FIG. 2, the second end 18 can be generally rectangular. The second end 18 can include a screw receiving member 26 and an insertion aperture 28. The screw receiving member 26 can be coupled to a distalmost end of the second end 18. The screw receiving member 26 can be coupled to the second end 18 via any suitable technique, such as a snap-fit, press-fit, welding, the use of mechanical fasteners etc. In addition, the screw receiving member 26 can be integrally formed with the body 14 of the implant 10. The screw receiving member 26 can include at least one aperture or bore 32 for receipt of the at least one bone screw 12 and an inserter bore 34. In this example, the screw receiving member 26 can include a first bore 32a and a second bore 32b.

The first bore 32a and the second bore 32b can be formed on a respective projection 36a, 36b. The projections 36a, 36b can be separated by an opening or a gap, to enable an inserter to engage the inserter bore 34, as will be discussed in greater detail herein. In one example, the projections 36a, 36b can be formed so that the first bone screw 12a and second bone screw 12b be can be spaced about 1.0 millimeters (mm) apart. It should be noted that the use of the projections 36a, 36b is merely exemplary, as the first bore 32a and second bore 32b could be formed from a uniform portion of the screw receiving member 26, if desired. The projections 36a, 36b can be generally square, and can be angled relative to the body 14 of the implant 10, so that the first bore 32a and second bore 32b can be formed at an angle relative to the body 14 of the implant 10. Generally, the projections 36a, 36b can be angled relative to the body 14 so that the first bore 32a and second bore 32b pass through a minimal amount of the body 14 of the implant 10. It should be noted, however, that the projections 36a, 36b need not be formed at an angle as the first bore 32a and second bore 32b can extend through a portion of the implant 10, if desired. With reference to FIG. 3, the projections 36a, 36b can extend for a length L, which can be sized to enable a head 38a, 38b of the respective first bone screw 12a and second bone screw 12b to be retained within the respective one of the first bore 32a and second bore 32b when the first bone screw 12a and second bone screw 12b are coupled to the implant 10.

With reference to FIG. 3, the first bore 32a can be formed along an axis A1, which can be transverse to a longitudinal axis L of the body 14 of the implant 10. In one example, the axis A1 can be formed at about a 30 degree to about a 60 degree angle relative to a longitudinal axis L of the implant 10. The orientation of the axis A1 is merely exemplary, as the axis A1 could be oriented at any desired angle relative to the implant 10. The first bore 32a can include a sidewall 40 defining at least one or a plurality of threads 42. Thus, the first bore 32a can comprise a threaded bore. The sidewall 40 can be formed so as to extend circumferentially around only a portion of the first bore 32a. In other words, the first bore 32a can be formed with an open perimeter.

In one example, the sidewall 40 can circumferentially extend around about 120° to about 180° of the first bore 32a. Generally, the sidewall 40 circumferentially surrounds no more than 180° of the first bore 32a, so that the first bore 32a can circumferentially surround generally no more than 180° of the first bone screw 12a, as illustrated in FIG. 2. In other particular embodiments, the first bore 32a can circumferentially surround no more than 120° of the first bone screw 12a. In addition, the amount of the sidewall 40 that extends circumferentially around the first bore 32a can vary along the length of the first bore 32a, if desired. For example, the amount the sidewall 40 circumferentially surrounds the first bore 32a can be greater at a proximalmost end 44 of the first bore 32a than at a distalmost end 46 of the first bore 32a (FIG. 2). In the embodiment illustrated, the sidewall 40 circumferentially surrounds the first bore 32a no more than 180° at any point along the length.

With reference to FIG. 3, the plurality of threads 42 can be formed along the sidewall 40. The threads 42 can comprise an interlocking thread form. For example, the threads 42 can interlock with a corresponding thread form on the head 38a of the first bone screw 12a. One suitable thread form is commercially available from Biomet, Inc. of Warsaw, Ind., under the trademark Helical Flange®. It should be noted, however, that the threads 42 can include any suitable interlocking thread form. For example, with reference to FIG. 4, the threads 42 can include an interlocking feature 48. The interlocking feature 48 can comprise a lip or flange. The interlocking feature 48 can cooperate with a corresponding interlocking thread form on the head 38a of the first bone screw 12a to couple the first bone screw 12a to the first bore 32a. It should be noted that the interlocking feature 48 can have any desired shape or configuration that interlocks with a mating shape or configuration formed on the head 38a of the first bone screw 12a. For example, the interlocking feature 48 can comprise a rounded projection, a square projection, dovetail, etc. The interlocking feature 48 can be formed substantially along an entire length of the threads 42, however, the interlocking feature 48 can alternatively be formed along only a portion of the threads 42 sufficient to retain the first bone screw 12a to the body 14, if desired. Thus, the interlocking feature 48 illustrated herein will be understood to be merely exemplary.

In addition to the interlocking feature 48, the threads 42 can optionally include a locking mechanism generally indicated by reference numeral 50. In one example, with reference to FIG. 5A, the locking mechanism 50 can comprise a pitch 52 of the threads 42. In this example, the pitch 52 can be different than a pitch 54 of at least one or a plurality of threads 56 formed on the head 38a of the first bone screw 12a. The pitch 52 can be greater than or less than the pitch 54 of the threads 56 to cause the threads 42 and threads 56 to bind to further couple the first bone screw 12a to the implant 10. In one example, the pitch 52 of the threads 42 can be less than the pitch 54 of the threads 56. For example, the pitch 52 can be about 2.29 mm and the pitch 54 can be about 2.39 mm. It should be noted that the first bore 32a need not have the same pitch 52 along the length of the first bore 32a. Rather, the pitch 52 could be altered at a desired location on the first bore 32a to cause the threads 42 to bind with the threads 56 on the head 38a of the first bone screw 12a.

Figures 5A, 5B:
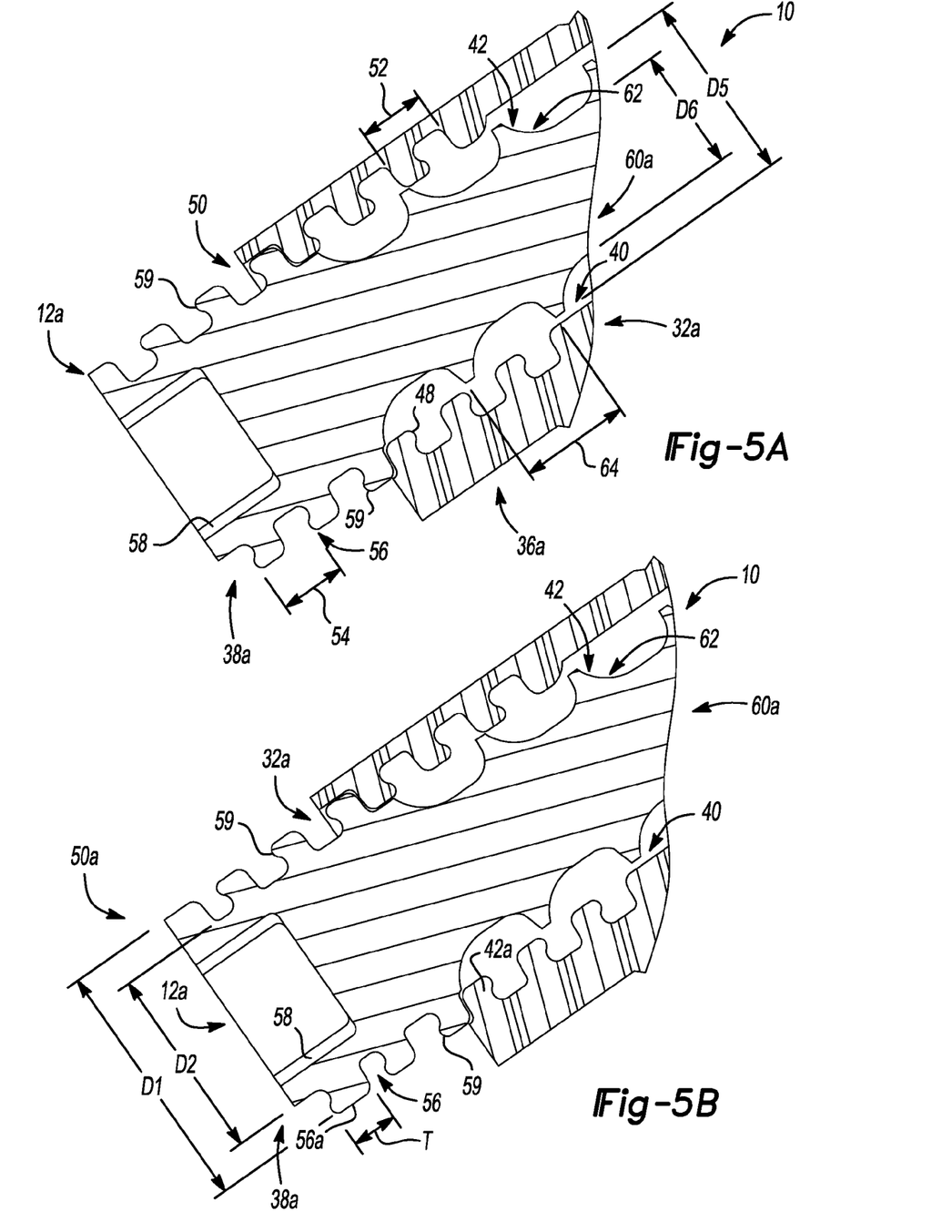
FIG. 5A is a cross-sectional view similar to FIG. 4, illustrating an exemplary locking mechanism between an exemplary bone fastener and the exemplary implant.
FIG. 5B is another cross-sectional view similar to FIG. 4, illustrating another exemplary locking mechanism between an exemplary bone fastener and the exemplary implant.

In an alternative example, with reference to FIG. 5B, the threads 42 can include a locking mechanism 50a. The locking mechanism 50a can comprise an interference that causes the threads 42 to bind with the threads 56 of the head 38a. In one example, the locking mechanism 50a can comprise an increased thickness T of a proximalmost thread 56a of the head 38a. Further, it should be noted that various techniques could be used to cause an interference between the threads 42 and threads 56 of the head 38a besides the use of the proximalmost thread 56a with increased thickness. For example, a portion of a proximalmost thread 42a of the threads 42 could include a slight outward projection, which could interfere with a similar outward projection formed on the proximalmost thread 56a of the head 38a. It should be noted that the location of the interference is merely exemplary, as the interference could be caused at any selected location along the threads 42 and threads 56.

As a further example, a major diameter D1 of the proximalmost thread 56a can be varied to cause an interference upon the advancement of the first bone screw 12a into the first bore 32a. In one example, the major diameter D1 can be greater at the proximalmost thread 56a as compared to the rest of the threads 56 to cause an interference at the proximalmost thread 56a when the first bone screw 12a is advanced into the first bore 32a. The interference can further couple the first bone screw 12a to the implant 10. Alternatively, a minor diameter D2 of the proximalmost thread 56a can be varied to assist in coupling the first bone screw 12a to the implant 10. For example, the minor diameter D2 can be greater at the proximalmost thread 56a as compared to the rest of the threads 56 to cause an interference at the proximalmost thread 56a when the first bone screw 12a is advanced into the first bore 32a. It should be noted that the location of the varied diameter for the major diameter D1 and minor diameter D2 is merely exemplary as the variation could occur at any selected location along the length of the first bone screw 12a.

According to another alternative example, a taper can be formed on the sidewall 40 and a taper can be formed on the head 38a of the first bone screw 12a. The taper can be formed such that the largest diameter of the taper is near the proximalmost thread 42a and the taper can be formed such that the largest diameter of the taper is near the proximalmost thread 56a of the threads 56. The use of the tapers can cause the threads 42, 56 to bind to further couple the first bone screw 12a to the implant 10.

With reference to FIGS. 2 and 3, the second bore 32b can receive the second bone screw 12b. As the second bore 32b can be similar to the first bore 32a, only the differences between the first bore 32a and the second bore 32b will be discussed in great detail herein, and the same reference numerals will be used to denote the same or similar components. With reference to FIG. 2, the second bore 32b can be formed along an axis A2, which can be transverse to the longitudinal axis L of the body 14 of the implant 10. The axis A2 can be formed at about a negative 30 degree to about a negative 60 degree angle relative to the longitudinal axis L of the implant 10. The orientation of the axis A2 is merely exemplary, as the axis A2 could be oriented at any desired angle relative to the implant 10. The second bore 32b can include the sidewall 40 defining the at least one or plurality of threads 42. Thus, the second bore 32b can comprise a threaded bore.

In one example, as illustrated in FIG. 2, the sidewall 40 of the second bore 32b can be formed so as to extend circumferentially around only a portion of the second bore 32b. In other words, the second bore 32b can be formed with an open perimeter. In one example, the sidewall 40 can circumferentially extend around about 120° to about 180° of the second bore 32b. Generally, the sidewall 40 circumferentially surrounds no more than 180° of the second bore 32b, so that the second bore 32b can circumferentially surround generally no more than 180° of the second bone screw 12b. In other particular embodiments, the second bore 32b can circumferentially surround no more than 120° of the second bone screw 12b. In addition, the amount of the sidewall 40 that extends circumferentially around the second bore 32b can vary along the length of the second bore 32b, if desired. For example, the amount the sidewall 40 circumferentially surrounds the second bore 32b can be greater at the proximalmost end 44 of the second bore 32b than at the distalmost end 46 of the second bore 32b. In the embodiment illustrated, the sidewall 40 surrounds the second bore 32b no more than 180° at any point along the length. The threads 42 of the second bore 32b can also optionally include the locking mechanism 50 or locking mechanism 50a as discussed with regard to FIGS. 5A and 5B.

Thus, the second bore 32b can be substantially similar to or the same as the first bore 32a. It should be noted, however, that one of the first bore 32a and second bore 32b could include a sidewall that circumferentially surrounds about 360° of the respective first bore 32a or second bore 32b, if desired. Further, any combination of locking mechanisms 50, 50a could be employed with the first bore 32a and second bore 32b, and thus, the same locking mechanism 50, 50a need not be employed in both the first bore 32a and second bore 32b. In addition, the locking mechanism 50, 50a could be used in only one of the first bore 32a and second bore 32b, if desired. It should also be noted that although the implant 10 is described and illustrated herein as including a first bore 32a and a second bore 32b, the implant 10 could include any number of bores 32.

With reference to FIG. 2, the inserter bore 34 can be defined between the first projection 36a and second projection 36b. The inserter bore 34 can be in communication with the insertion aperture 28. The inserter bore 34, insertion aperture 28 and aperture 20 can enable an insertion tool to be coupled to the implant 10 to guide the implant 10 through the anatomy for placement of the implant 10 at a desired location within the anatomy.

With regard to FIG. 2, the first bone screw 12a and second bone screw 12b can be received through a respective one of the first bore 32a and second bore 32b. The first bone screw 12a and second bone screw 12b can be formed of a suitable biocompatible material, such as a biocompatible metal, metal alloy or polymer. In one example, the first bone screw 12a and second bone screw 12b can be composed of titanium. The first bone screw 12a and the second bone screw 12b can be substantially similar or the same. The first bone screw 12a and second bone screw 12b can include the heads 38a, 38b and can also include a respective shank 60a, 60b. The heads 38a, 38b can include the threads 56 and a driver engagement feature 58. The driver engagement feature 58 can enable the first bone screw 12a and the second bone screw 12b to be driven by a suitable instrument.

The threads 56 can be formed about the circumference of the heads 38a, 38b, and can comprise any suitable interlocking thread form. The threads 56 can include an interlocking feature 59. The interlocking feature 59 can cooperate with the interlocking feature 48 of the threads 42 to enable the threads 42 and threads 56 to interlock. The interlocking feature 59 can comprise a recess, which can receive the lip or flange of the interlocking feature 48. It should be noted that the interlocking feature 59 can have any desired shape or configuration that interlocks with a mating shape or configuration formed on the threads 42 of the first bore 32a and second bore 32b. For example, the interlocking feature 59 can comprise a rounded recess, a square recess, dovetail, etc. The interlocking feature 59 can be formed substantially along an entire length of the threads 56, however, the interlocking feature 59 could be formed along only a portion of the threads 56, if desired. Thus, the interlocking feature 59 illustrated herein is merely exemplary.

The shank 60a, 60b can extend from the heads 38a, 38b. The shank 60a, 60b can include at least one or a plurality of threads 62. With reference to FIG. 5A, the threads 62 can have a pitch 64, which can be different than or equal to the pitch 54 of the heads 38a, 38b. In one example, the pitch 64 can be different than the pitch 54 of the heads 38a, 38b. The threads 62 can also include a major diameter D5 and a minor diameter D6. In one example, the major diameter D5 can be different than the major diameter D1 of the threads 56 of the head 38a, 38b. The minor diameter D6 can be different than the minor diameter D2 of the threads 56 of the head 38a, 38b. In one example, the minor diameter D6 can be less than the major diameter D4 of the threads 42 of the first bore 32a and second bore 32b, and can also be less than the major diameter D2 of the threads 56 of the head 38a, 38b.

According to one exemplary method, with reference to FIG. 1, the implant 10 can be inserted into the anatomy. The implant 10 can be inserted into the anatomy via any suitable technique. As the insertion of the implant 10 into the anatomy is beyond the scope of the present disclosure, and the insertion of the implant 10 will not be discussed in great detail herein. In one example, with access gained to the desired implantation site, an insertion tool can be coupled to the inserter bore 34 and insertion aperture 28. Then, the insertion tool can be used to guide the implant 10 through the anatomy to the desired implantation site.

Once the implant 10 is positioned as desired between the endplates of adjacent vertebrae V, with reference to FIG. 2, the first bone screw 12a can be threadably inserted into the first bore 32a. The first bone screw 12a can be inserted through the first bore 32a until the head 38a is retained within the first bore 32a, or until the locking mechanism 50, 50a prevents the further travel of the first bone screw 12a. In the example of the locking mechanism 50, the difference between the pitch 52 of the threads 42 and the pitch 54 of the threads 56 can cause the threads 42 and threads 56 to bind as the first bone screw 12a advances through the first bore 32a (FIG. 5A). The binding of the threads 42 and threads 56 can further secure the first bone screw 12a to the implant 10.

In the example of the locking mechanism 50a, the increased thickness T of the proximalmost thread 56a can interfere with the further advancement of the first bone screw 12a through the first bore 32a, thereby further coupling the first bone screw 12a to the implant 10 (FIG. 5B).

With the first bone screw 12a coupled to the implant 10, the second bone screw 12b can be coupled to the implant 10. The second bone screw 12b can be threadably inserted into the second bore 32b (FIG. 2). The second bone screw 12b can be inserted through the second bore 32b until the head 38b is retained within the second bore 32b, or until the locking mechanism 50, 50a prevents the further travel of the second bone screw 12b. The use of the locking mechanism 50, 50a can further secure the second bone screw 12b to the implant 10.

Figure 6:
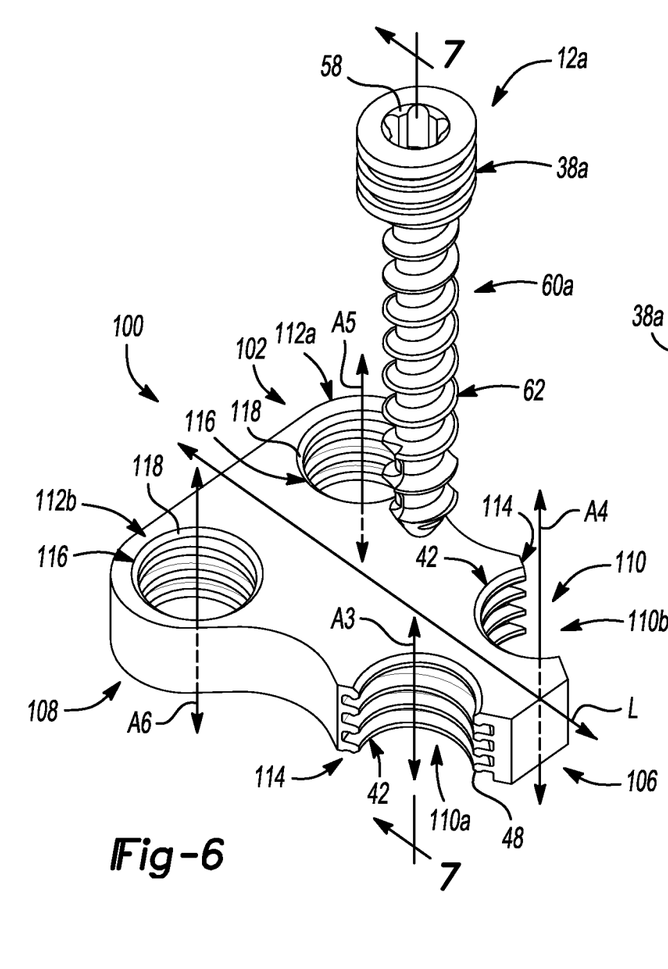
FIG. 6 is an exploded perspective view of another exemplary implant with semi-enclosed screws according to the present teachings.
Figure 7:
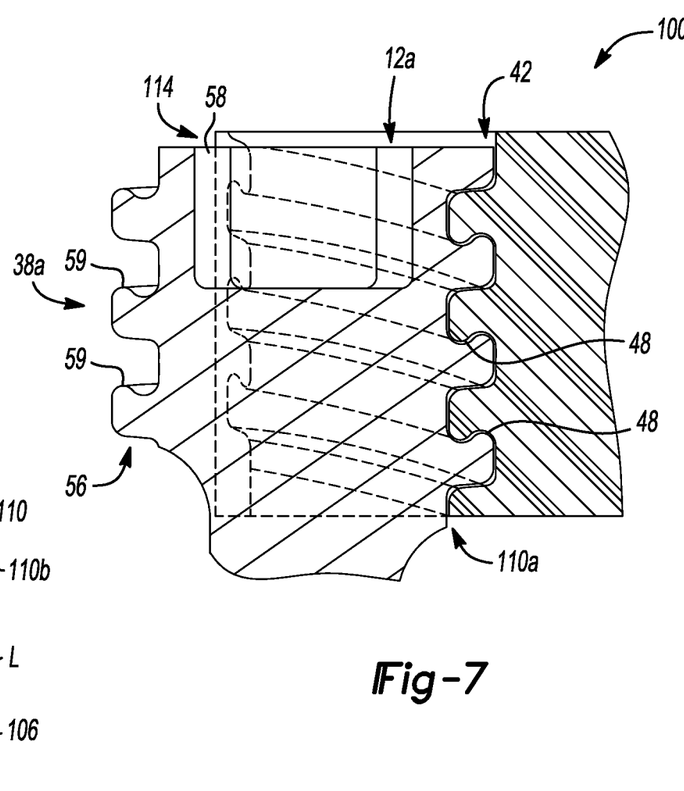
FIG. 7 is a cross-sectional view of the implant of FIG. 6, taken along line 7-7 of FIG. 6.

With reference now to FIGS. 6-7, in one example, an implant 100 can be employed with at least one of the first bone screw 12a and second bone screw 12b to repair a damaged portion of an anatomy. As the implant 100 can be similar to the implant 10 described with reference to FIGS. 1-5B, only the differences between the implant 10 and the implant 100 will be discussed in great detail herein, and the same reference numerals will be used to denote the same or similar components. In this example, the implant 100 can comprise a bone plate, such as an occipital plate, for repairing a damaged portion of the spinal column. It should be noted that although the implant 100 is described and illustrated herein as a bone plate for use in the spinal column, the teachings of the implant 100 can be applied to any suitable bone plate, such as a bone plate for use in repairing a distal humerus. In one example, the implant 100 can include a body 102.

With reference to FIG. 6, the body 102 of the implant 100 can be formed from any suitable biocompatible material, such as a biocompatible metal, metal alloy or polymer. For example, the body 102 can be composed of polyether ether ketone (PEEK), but the body 102 could also be formed of titanium. The body 102 can have a generally triangular shape, and can have a first end 106 and a second end 108. The first end 106 can include at least one bore 110, and the second end 108 can include at least one bore 112. In this example, the first end 106 can include a first bore 110a and a second bore 110b, and the second end 108 can include a third bore 112a and a fourth bore 112b. It should be noted that the first end 106 could include only one of the first bore 110a and second bore 110b, if desired. Similarly, the second end 108 could include only one of the third bore 112a and the fourth bore 112b, or could include additional bores, if desired.

The first bore 110a can be formed along an axis A3, which in this example, can be transverse or substantially perpendicular to a longitudinal axis L of the body 102. The orientation of the axis A3 is merely exemplary, as the axis A3 could be oriented at any desired angle relative to the implant 100. The first bore 110a can include a sidewall 114 defining at least one or the plurality of threads 42. Thus, the first bore 110a can comprise a threaded bore. The sidewall 114 can be formed so as to extend circumferentially around only a portion of the first bore 110a. In other words, the first bore 110a can be formed with an open perimeter. In one example, the sidewall 114 can circumferentially extend around about 120° to about 180° of the first bore 110a. Generally, the sidewall 114 circumferentially surrounds no more than 180° of the first bore 110a, so that the first bore 110a can circumferentially surround generally no more than 180° of the bone screw 12a. In other particular embodiments, the first bore 110a can circumferentially surround no more than 120° of the first bone screw 12a. In addition, the amount of the sidewall 114 that extends circumferentially around the first bore 110a can vary along the length of the first bore 110a, if desired. In the embodiment illustrated, the sidewall 114 circumferentially surrounds the first bore 110a no more than 180° at any point along the length.

The plurality of threads 42 can be formed along the sidewall 114. The threads 42 can comprise the interlocking thread form, with the interlocking feature 48. The interlocking feature 48 can cooperate with the threads 56 on the head 38a of the first bone screw 12a to couple the first bone screw 12a to the first bore 110a. Optionally, the threads 42 can include the locking mechanism 50, the locking mechanism 50a, or any suitable locking mechanism described herein with reference to FIGS. 1-5B.

The second bore 110b can receive a second bone screw 12b. As the second bore 110b can be substantially similar to the first bore 110a, only the differences between the first bore 32a and the second bore 32b will be discussed in great detail herein, and the same reference numerals will be used to denote the same or similar components. The second bore 110b can be formed along an axis A4. The axis A4 can be substantially parallel to the axis A3, and transverse or substantially perpendicular to the longitudinal axis L of the implant 100. The orientation of the axis A4 is merely exemplary, as the axis A4 could be oriented at any desired angle relative to the axis A3 and implant 100. The second bore 110b can include the sidewall 114 defining the at least one or plurality of threads 42. Thus, the second bore 110b can comprise a threaded bore.

In one example, the sidewall 114 of the second bore 110b can be formed so as to extend circumferentially around only a portion of the second bore 110b. In other words, the second bore 110b can be formed with an open perimeter. In one example, the sidewall 114 can circumferentially extend around about 120° to about 180° of the second bore 110b. Generally, the sidewall 114 circumferentially surrounds no more than 180° of the second bore 110b, so that the second bore 110b can circumferentially surround generally no more than 180° of the second bone screw 12b. In other particular embodiments, the second bore 110b can circumferentially surround no more than 120° of the second bone screw 12b. In addition, the amount of the sidewall 114 that extends circumferentially around the second bore 110b can vary along a length L4 of the second bore 110b, if desired. In the embodiment illustrated, the sidewall 114 circumferentially surrounds the second bore 110b no more than 180° at any point along the length. The threads 42 can include the optional locking mechanism 50, the locking mechanism 50a, or any suitable locking mechanism described herein with reference to FIGS. 1-5B.

With reference to FIG. 6, the second end 108 can include the third bore 112a and the fourth bore 112b. The third bore 112a and fourth bore 112b can be formed along an axis A5 and an axis A6, respectively, which in this example, can be substantially transverse or perpendicular to a longitudinal axis L of the body 102. The orientation of the axes A5, A6 is merely exemplary, as the axes A5, A6 could be oriented at any desired angle relative to the implant 100. The third bore 112a and fourth bore 112b can include a sidewall 116 defining at least one or a plurality of threads 118. Thus, the third bore 112a and fourth bore 112b can comprise threaded bores. The threads 118 can comprise interlocking or non-interlocking threads. In one example, the threads 118 can be non-interlocking threads, which can engage a threaded head of a bone fastener or bone screw. The sidewall 116 can be formed so as to extend around the entire circumference of the third bore 112a and fourth bore 112b. In other words, the third bore 112a and fourth bore 112b can each be formed with a closed perimeter. It should be noted, however, that the second end 108 can include one or more of the first bore 110a or second bore 110b having an open perimeter, if desired.

According to one exemplary method, the implant 100 can be inserted into the anatomy. The implant 100 can be inserted into the anatomy via any suitable technique. As the insertion of the implant 100 into the anatomy is beyond the scope of the present disclosure, and the insertion of the implant 100 will not be discussed in great detail herein. In one example, the implant 100 can be positioned against the desired vertebrae within the anatomy. Then, the first bone screw 12a can be threadably inserted into the first bore 110a. The first bone screw 12a can be inserted through the first bore 110a until the head 38a is retained within the first bore 110a, or until the locking mechanism 50, 50a prevents the further travel of the first bone screw 12a. In the example of the locking mechanism 50, the difference between the pitch 52 of the threads 42 and the pitch 54 of the threads 56 can cause the threads 42 and threads 56 to bind as the first bone screw 12a advances through the first bore 110a. The binding of the threads 42 and threads 56 can further secure the first bone screw 12a to the implant 100.

In the example of the locking mechanism 50a, the increased thickness T of the proximalmost thread 56a can interfere with the further advancement of the first bone screw 12a through the first bore 110a, thereby further coupling the first bone screw 12a to the implant 100.

With the first bone screw 12a coupled to the implant 100, a second bone screw 12b can be coupled to the implant 100. Similarly, the second bone screw 12b can be threadably inserted into the second bore 110b. The second bone screw 12b can be inserted through the second bore 110b until the head 38b is retained within the second bore 110b, or until the locking mechanism 50, 50a prevents the further travel of the second bone screw 12b. The use of the locking mechanism 50, 50a can further secure the second bone screw 12b to the implant 100. Additional bone screws can be inserted through the third bore 112a and fourth bore 112b to couple the implant 100 to the anatomy.

It should be noted that the implant 10, 100 can be available as a kit, which can include any number of bone fasteners, such as the first bone screw 12a and second bone screw 12b. The use of the first bore 32a, 110a and second bore 32b, 110b can enable fixation of the implant 10, 100 to the anatomy with only a minimal amount of the first bone screw 12a and second bone screw 12b passing through the body 14, 102 of the implants 10, 100. The first bone screw 12a and second bone screw 12b can be positively engaged to the implant 10, 100 through cooperation of the first bore 32a, 110a and second bore 32b, 110b and the threaded head 38a, 38b of the first bone screw 12a and second bone screw 12b. In addition, the use of the first bore 32a, 110a and second bore 32b, 110b can enable greater spacing between the first bone screw 12a and second bone screw 12b as the first bone screw 12a and second bone screw 12b do not need to pass entirely though the body 14, 102 of the implant 10, 100. The greater spacing between the first bore 32a, 110a and second bore 32b, 110b can assist in the insertion and fixation of the implant 10, 100 within the anatomy. This can provide the surgeon with greater flexibility in performing a surgical procedure.

While specific examples have been described in the specification and illustrated in the drawings, it will be understood by those of ordinary skill in the art that various changes can be made and equivalents can be substituted for elements thereof without departing from the scope of the present teachings. Furthermore, the mixing and matching of features, elements and/or functions between various examples is expressly contemplated herein so that one of ordinary skill in the art would appreciate from the present teachings that features, elements and/or functions of one example can be incorporated into another example as appropriate, unless described otherwise, above. Moreover, many modifications can be made to adapt a particular situation or material to the present teachings without departing from the essential scope thereof. Therefore, it is intended that the present teachings not be limited to the particular examples illustrated by the drawings and described in the specification, but that the scope of the present teachings will include any embodiments falling within the foregoing description.

What is claimed is:

1. An implant comprising:
   an implant body partially defining at least one threaded aperture; and
   a bone fastener including a threaded portion threadably engaged with the at least one threaded aperture,
   wherein the at least one threaded aperture circumferentially surrounds no more than 180° of the bone fastener along the entire length of the at least one threaded aperture and includes an open perimeter of at least 180° along the entire length of the at least one threaded aperture, and
   wherein the at least one threaded aperture includes a first threaded aperture extending along a first axis substantially transverse to a longitudinal axis of the implant body and a second threaded aperture extending along a second axis substantially transverse to the longitudinal axis of the implant, the first axis transverse to the second axis.

2. The implant of claim 1, wherein the bone fastener is positively engaged to the implant in a radial direction through cooperation of the at least one threaded aperture and the threaded portion.

3. The implant of claim 1, wherein the bone fastener further comprises a head and a shank, and the threaded portion is defined on the head of the bone fastener.

4. The implant of claim 1, wherein the threaded aperture is threaded with a first interlocking thread form and the threaded portion is threaded with a second interlocking threaded form.

5. The implant of claim 4, wherein the first interlocking thread form has a first pitch and the second interlocking thread form has a second pitch, the second pitch being different than the first pitch along at least a portion of the threaded portion.

6. The implant of claim 1, wherein the implant is an intervertebral implant.

7. The implant of claim 1, wherein the implant is a bone plate.

8. The implant of claim 1, wherein the threaded aperture circumferentially surrounds between 120° to 170° of the bone fastener.

9. The implant of claim 1, wherein the implant body includes a first projection extending along the first axis, and wherein the first threaded aperture extends at least partially through the first projection.

10. The implant of claim 1, wherein the implant includes a top side and a pair of lateral sides, the first and second threaded apertures both open to the top side and one of the lateral sides.

11. An implant comprising:
an implant body partially defining at least one aperture extending along a first axis, the at least one aperture having an open perimeter of at least 180° along the entire length of the at least one aperture and a first plurality of threads, the first plurality of threads including a first axially extending lip; and
a bone fastener including a head having a second plurality of threads threadably engaged with the first plurality of threads of the at least one aperture, the second plurality of threads including a second axially extending lip,
wherein the first axially extending lip interlocks with the second axially extending lip,
wherein the implant body includes a first projection extending along a first axis substantially transverse to a longitudinal axis of the implant body, and wherein the at least one aperture extends along the first axis at least partially through the first projection, and
wherein an interlocking connection between the bone fastener and the at least one aperture prevents displacement of the bone fastener relative to the at least one aperture in a radial direction.

12. The implant of claim 11, wherein the at least one aperture circumferentially surrounds no more than 180° of the bone fastener along the entire length of the at least one aperture.

13. The implant of claim 11, wherein the at least one aperture circumferentially surrounds between 120° to 180° of the bone fastener along the entire length of the at least one aperture.

14. The implant of claim 11, wherein the first plurality of threads and the second plurality of threads include a locking mechanism.

15. The implant of claim 14, wherein the locking mechanism further comprises a variation between a first pitch of the first plurality of threads and a second pitch of the second plurality of threads.

16. The implant of claim 15, wherein the second pitch is different than the first pitch along at least a portion of the head of the bone fastener.

17. The implant of claim 14, wherein the locking mechanism is an interference between the first plurality of threads and second plurality of threads.

18. The implant of claim 17, wherein the interference further comprises a difference between a diameter of a portion of the first plurality of threads and a diameter of a portion of the second plurality of threads.

19. The implant of claim 17, wherein the interference further comprises an increased thickness of a portion of at least one of the first plurality of threads and second plurality of threads.

20. An implant comprising:
an implant body partially defining at least one aperture having a first interlocking thread form that circumferentially surrounds no more than 180° along the entire length of the at least one aperture, and includes an open perimeter of at least 180° along the entire length of the at least one aperture; and
at least one bone fastener including a head having a second interlocking thread form interlocked and threadably engaged with the first interlocking thread form of the at least one aperture,
wherein a pitch of the first interlocking thread form is different than a pitch of the second interlocking thread form.

21. The implant of claim 20, wherein the at least one aperture circumferentially surrounds between 120° to 180° of the bone fastener.

22. The implant of claim 20, wherein an interlocking connection between the at least one bone fastener and the at least one aperture prevents displacement of the at least one bone fastener relative the at least one aperture in a radial direction.

23. The implant of claim 20, wherein the implant body includes a top side and a pair of lateral sides, each of the at least one aperture open to the top side and one of the lateral sides.

24. The implant of claim 20, wherein the at least one aperture includes a first aperture on a first side of a longitudinal axis of the implant and a second aperture on a second side of the longitudinal axis, and
wherein the first aperture includes an open perimeter with at least a portion of the opening facing away from a centerline of the implant, and the second aperture includes an open perimeter with at least a portion of the opening facing in an opposing direction away from the centerline of the implant.

* * * * *